(12) United States Patent
Mohtadi et al.

(10) Patent No.: US 8,771,635 B2
(45) Date of Patent: Jul. 8, 2014

(54) HYDROGEN RELEASE FROM COMPLEX METAL HYDRIDES BY SOLVATION IN IONIC LIQUIDS

(75) Inventors: Rana F. Mohtadi, Northville, MI (US); PremKumar Sivasubramanian, Ann Arbor, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 437 days.

(21) Appl. No.: 13/094,464

(22) Filed: Apr. 26, 2011

(65) Prior Publication Data
US 2011/0280797 A1 Nov. 17, 2011

Related U.S. Application Data

(60) Provisional application No. 61/327,764, filed on Apr. 26, 2010.

(51) Int. Cl.
*C01B 3/04* (2006.01)
*C01B 6/04* (2006.01)
*C01B 6/02* (2006.01)

(52) U.S. Cl.
USPC .................. 423/648.1; 252/184; 423/644

(58) Field of Classification Search
USPC .................. 423/648.1, 644; 252/184
See application file for complete search history.

(56) References Cited

U.S. PATENT DOCUMENTS

| | | | |
|---|---|---|---|
| 6,534,033 B1 | 3/2003 | Amendola et al. | |
| 7,214,439 B2 | 5/2007 | Ortega et al. | |
| 7,563,308 B2 | 7/2009 | Tempel et al. | |
| 2005/0069486 A1 | 3/2005 | Shaw | |
| 2006/0102489 A1 | 5/2006 | Kelly | |
| 2007/0283623 A1 | 12/2007 | Blencoe et al. | |
| 2010/0068134 A1* | 3/2010 | Sudik et al. ............ | 423/658.2 |

FOREIGN PATENT DOCUMENTS

WO 2009072989 A2 6/2009

OTHER PUBLICATIONS

International Search Report fo corresponding PCT/US2011/033978 dated Jan. 17, 2012; 3 pgs.

* cited by examiner

*Primary Examiner* — Wayne Langel
*Assistant Examiner* — Syed Iqbal
(74) *Attorney, Agent, or Firm* — Gifford, Krass, Sprinkle, Anderson & Citkowski, P.C.

(57) ABSTRACT

A hydrogen release material includes a complex metal hydride and an ionic liquid wherein the hydrogen release material has a lower hydrogen release temperature in comparison to the complex metal hydride alone. Also disclosed is a process of releasing hydrogen from a storage material including the steps of: providing a complex metal hydride; combining the metal hydride with an ionic liquid in a desired amount forming a mixture; and heating the mixture to a temperature releasing hydrogen wherein the temperature is lower in comparison to the complex metal hydride alone.

25 Claims, 5 Drawing Sheets

HYDROGEN RELEASE FROM COMPLEX METAL HYDRIDES BY SOLVATION IN IONIC LIQUIDS

RELATED APPLICATIONS

This application claims priority of U.S. Provisional Patent Application Ser. No. 61/327,764 filed Apr. 26, 2010, which is incorporated herein by reference.

FIELD OF THE INVENTION

The invention relates to hydrogen storage materials.

BACKGROUND OF THE INVENTION

Current technologies utilized for gaseous hydrogen storage are limited by the low volume storage gas density at high pressures including pressures in the range of 5,000 to 10,000 psi. The energy density by volume of a gaseous hydrogen is less than that of a gasoline energy density. Use of hydrogen as an alternate fuel source is limited due to this lower energy density. Cryogenic storage of hydrogen at temperatures of around 20° Kelvin may improve the volumetric energy density compared to gasoline storage. However, production of liquid hydrogen is energy intensive and requires special storage and maintenance considerations to avoid hydrogen boil off.

Chemical storage of hydrogen in a solid form such as in a borohydride allows for hydrogen release when heated or mixed with water. However, formation of solid byproducts and release of hydrogen at very high temperatures, due to high activation barrier or thermodynamic stability, limit the use of such materials. Additionally, typically borohydrides are not able to be rehydrogenated at temperatures and pressures appropriate for on board hydrogen storage after hydrogen release.

There is therefore a need in the art for an improved hydrogen storage material that releases hydrogen at lower temperatures and is able to be rehydrogenated after release of the hydrogen.

SUMMARY OF THE INVENTION

In one aspect, there is disclosed a hydrogen release material that includes a complex metal hydride and an ionic liquid wherein the hydrogen release material has a lower hydrogen release temperature in comparison to the complex metal hydride alone.

In another aspect, there is disclosed a process of releasing hydrogen from a storage material including the steps of: providing a complex metal hydride; combining the metal hydride with an ionic liquid in a desired amount forming a mixture; and heating the mixture to a temperature releasing hydrogen wherein the temperature is lower in comparison to the complex metal hydride alone.

DETAILED DESCRIPTION OF THE INVENTION

Figure 1:
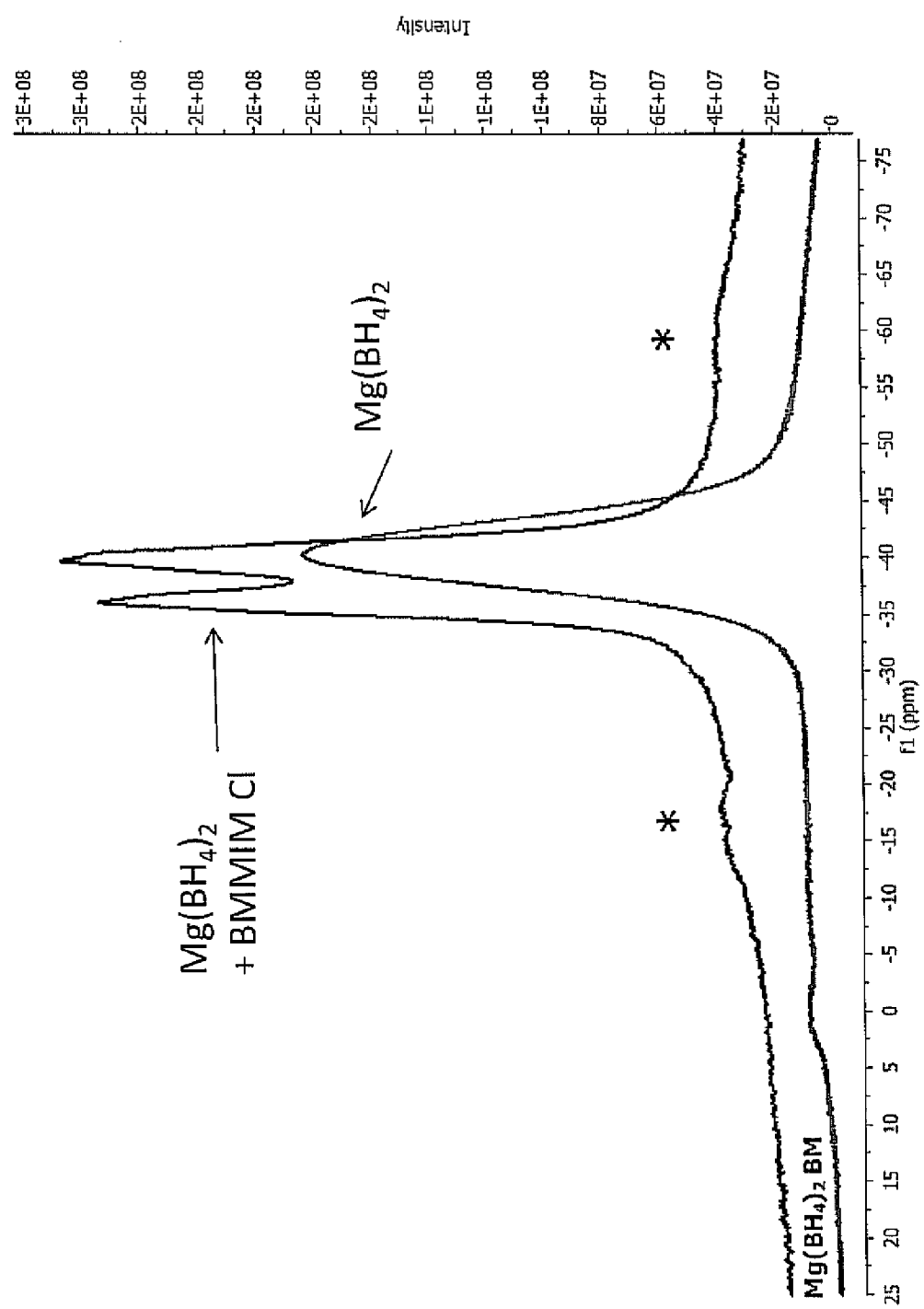
FIG. 1 is a NMR plot of a sample of magnesium borohydride and a sample of magnesium borohydride in an ionic liquid (1-butyl-2,3-dimethylimidazolium chloride)

In one aspect, there is disclosed a hydrogen release or storage material that includes a complex metal hydride and an ionic liquid. The hydrogen release material has a lower hydrogen release temperature than the complex metal hydride alone. Additionally, the hydrogen release material has a faster rate of hydrogen release and displays a reduction in activation barriers for hydrogen release.

The complex metal hydride may be a metal borohydride where the metal may be an alkali metal or an alkaline earth metal. The material may have the formula $M(BH_4)_x$ where M is an alkali metal or an alkaline earth metal and $1 \leq x \leq 2$. Various metal borohydrides including magnesium borohydride, lithium borohydride, sodium borohydride, potassium borohydride, or combinations of the above materials may be utilized. Additionally, various alkali earth metals may be included in the metal borohydride and be selected from magnesium, calcium, strontium, barium and mixtures of the above. Further the metal may be a transition metal of Group III of the periodic table. An example of a transition metal that may be utilized is scandium.

Additionally, the complex metal hydride may include a metal alanate of the formula $M(AlH_4)_x$ where $1 \leq x \leq 2$. Various alanates may be used where the metal is selected from an alkali metal or an alkaline earth metal and may include lithium alanate, sodium alanate, and magnesium alanate.

Various ionic liquids may be utilized to form the hydrogen release material. Examples of ionic liquids include N,N imidazolium or N-pyridinium or pyrrolidinium or piperidinium cations with various anions such as $AlCl_4^-$, $Al_2Cl_7^-$, $PF_6^-$, $BF_4^-$, $Cl^-$, $CF_3SO_3^-$, or other anions. Specifically, various ionic liquids including 1-butyl-2,3-dimethylimidazolium chloride, 1-butyl-3-methylimidazolium tetrafluoroborate, 1-butyl-3-methylimidazolium chloride, 1-butyl-3-methylimidazolium triflate, 1-butyl-3-methylimidazolium hexafluorophosphate, 1-ethyl-2,3-dimethylimidazolium ethyl sulfate, 1-ethyl-2,3-dimethyl imidazolium triflate, 1,3-dimethylimidazolium methylsulfate, 1-propyl-2,3-dimethylimidazolium triflide, 1-ethyl-3-methylimidazolium chloride, 1,2-dimethyl-3-n-butylimidazolium hexafluorophosphate, 1-methyl-1-butyl pyrrolidinium chloride, 1-methyl-1-butyl piperidinium [bis(trifluoromethylsulfonyl)imide as well as other materials may be utilized.

In one aspect, the complex metal hydride is solubilized in the ionic liquid thus forming cations and anions. The hydrogen release material is capable of reversible hydrogen storage. In one aspect, the ionic liquid has a weight percent of from 5 to 60 percent based on the total weight of the mixture.

There is disclosed a process of releasing hydrogen from a storage material that includes the steps of providing a complex metal hydride, grinding the complex metal hydride to a desired size, combining the ground complex metal hydride with an ionic liquid under agitation forming a mixture, and then heating the mixture to a temperature releasing hydrogen wherein the temperature is below the hydrogen release temperature of the complex metal hydride alone. As described above, the hydrogen release material includes a faster rate of hydrogen release as well as displays a reduction in activation barriers for hydrogen release. In another aspect, the ionic liquid may be dried or purified prior to combining with the metal hydride.

In one aspect, the ionic liquid and metal hydride may both be ground together in the grinding step. In one aspect, the combined ionic liquid and metal hydride may form a liquid or paste at room temperature. In another aspect, the ionic liquid may melt followed by hydrogen release at a temperature that is lower than the solid metal hydride material.

In another aspect, the ionic liquid may be in a liquid state. In one aspect, the complex metal hydride is solubilized in the ionic liquid which has a negligible vapor pressure and will not contaminate a fuel cell stack. Additionally, the liquid complex hydride mixture mitigates hydrogen formation reaction diffusion limitations and activation barriers that may be associated with a solid metal hydride material.

As described above, the hydrogen release material may be recharged or rehydrided after release of its initial hydrogen. The step of recharging may be performed at lower pressures and temperatures and occur at a faster rate than a complex metal hydride in solid form.

EXAMPLES

In the following examples magnesium borohydride, $Mg(BH_4)_2$ was ball milled and then combined with BMMIM Cl (1-butyl-2,3-dimethylimidazolium chloride). The $Mg(BH_4)_2$ and BMMIM Cl were combined at 51:49 wt % respectively. The BMMIM Cl was dried from water prior to combining by toluene azeotropic distillation and vacuum drying. The $Mg(BH_4)_2$ and BMMIM Cl were combined using mortar and pestle under argon gas atmosphere at room temperature. The sample was a paste at room temperature after combining. Analysis of the sample included NMR data obtained using Magic Angle Spinning MAS NMR as displayed in FIG. 1. Additionally the sample was analyzed in a thermogravimetric analyzer (Netzsch STA 409 PC) which had a residual gas analyzer attached to the vent line. The heating rate was 2° C./min and the ramp was from room temperature to 550° C.

Referring to FIG. 1 there is shown an NMR plot of a sample of $Mg(BH_4)_2$ in BMMIM Cl showing a double peak. The first double peak indicates a more mobile or less stable species that releases hydrogen at a lower temperature than the metal hydride alone which is represented by the second double peak that is in line with an NMR of magnesium borohydride as indicated in the plot. The sharp double peaks indicate a more mobile and less stable complex hydride anion which lowers an activation bather for hydrogen release in comparison to the complex metal hydride alone.

Figure 2:
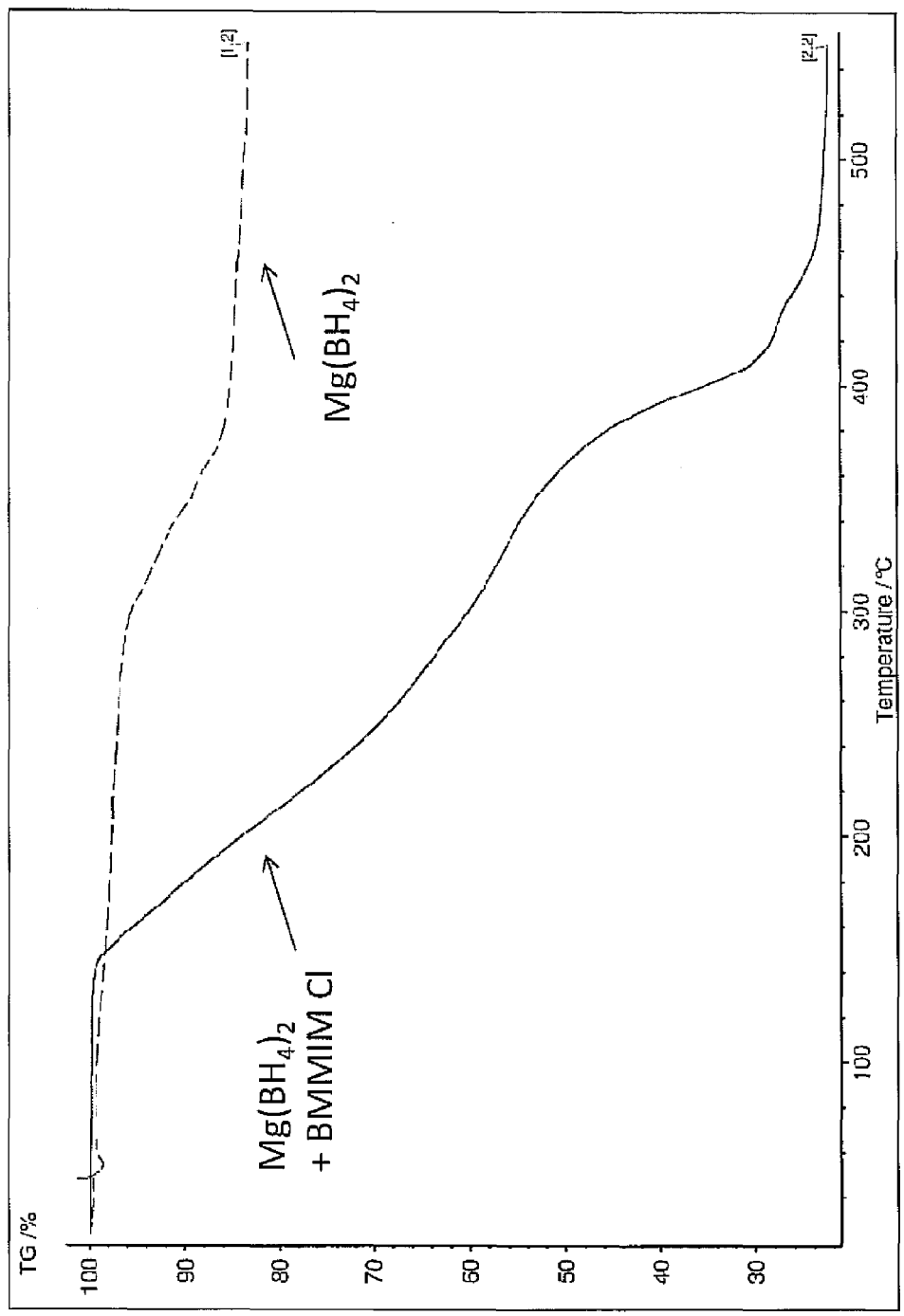
FIG. 2 is a plot of the TG % as a function of temperature for magnesium borohydride and magnesium borohydride in an ionic liquid (1-butyl-2,3-dimethylimidazolium chloride)
Figure 3:
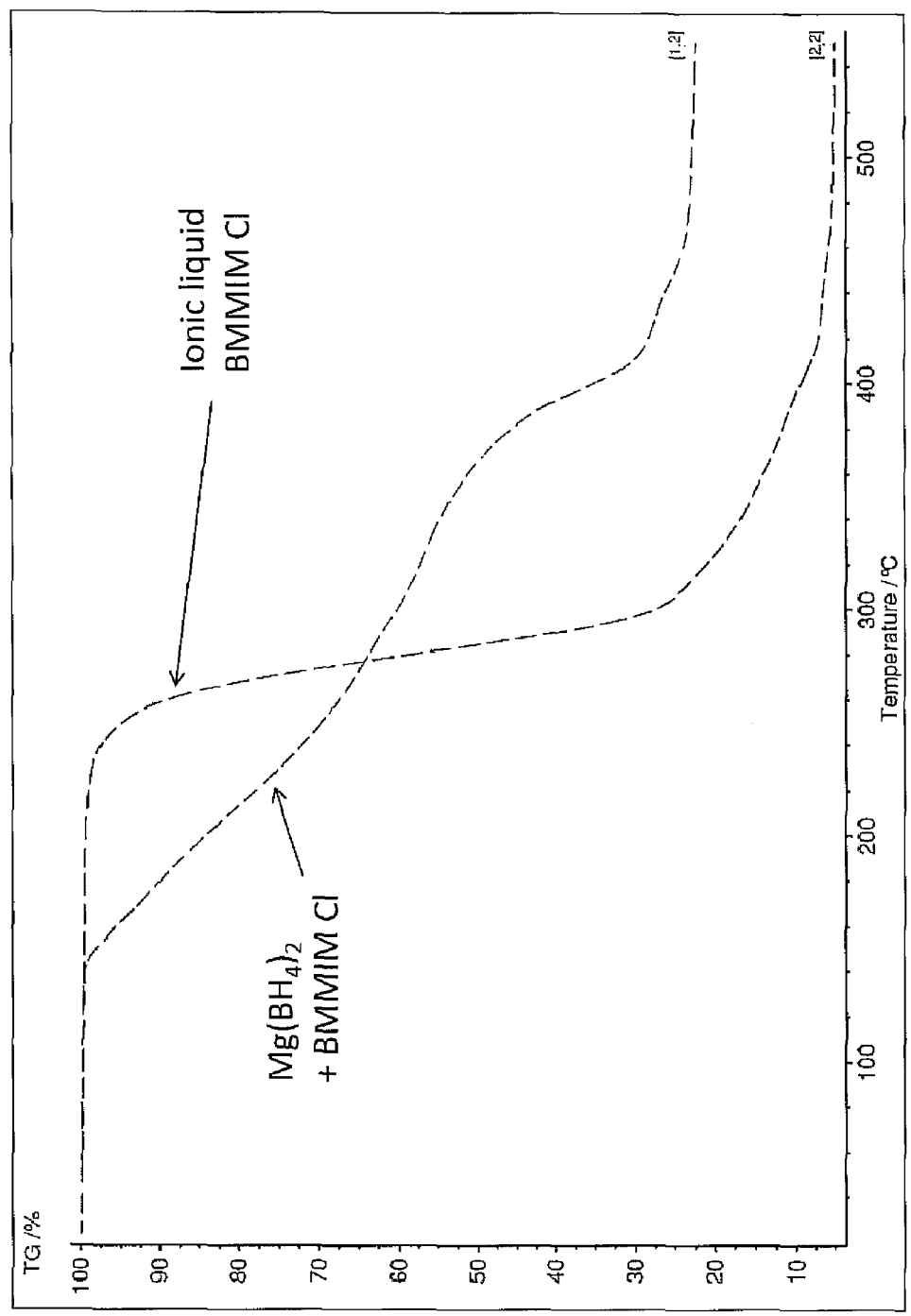
FIG. 3 is a plot of the TG % as a function of temperature for an ionic liquid (1-butyl-2,3-dimethylimidazolium chloride) and magnesium borohydride in an ionic liquid (1-butyl-2,3-dimethylimidazolium chloride)

Referring to FIG. 2, there is shown a plot of a pure magnesium borohydride sample and a sample of the magnesium borohydride combined with the ionic liquid as described above. As can be seen by the plot, the combined sample displayed a weight loss due to hydrogen evolution at a temperature of about 141 degrees C. whereas the pure magnesium borohydride sample shows a weight loss at about 295 degrees C. The significant difference in temperature of the weight loss indicates a greater than 50% difference in hydrogen release temperature. As indicated in FIG. 3, the combined sample evolves hydrogen at around 141 degrees C. which is lower than a decomposition temperature of the ionic liquid of about 260 degrees C.

Figure 4:
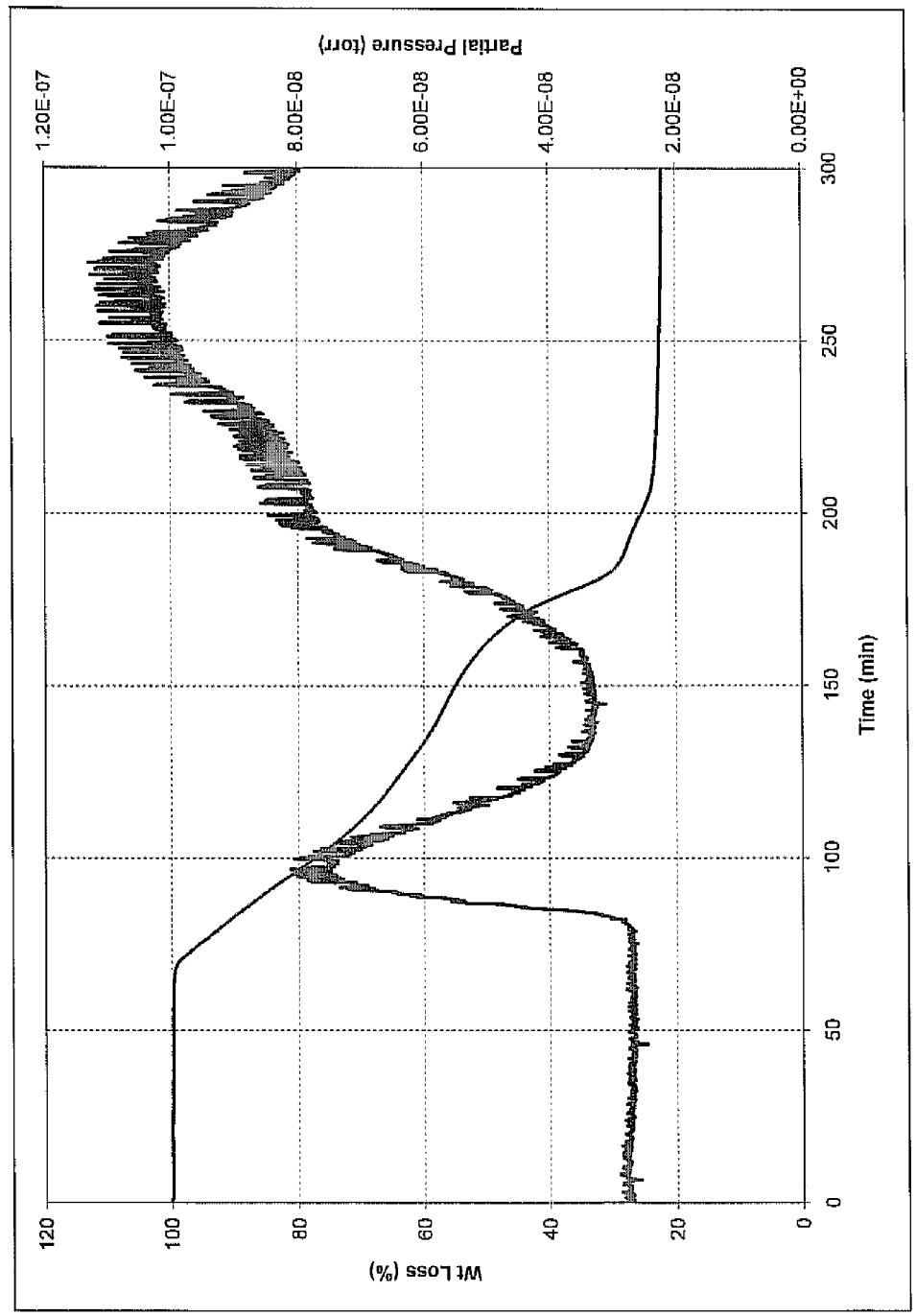
FIG. 4 is a plot of the partial pressure and weight loss % as a function of time for magnesium borohydride in an ionic liquid (1-butyl-2,3-dimethylimidazolium chloride)

Referring to FIG. 4, there is shown a plot indicating release of hydrogen from the combined sample. As can be seen in the plot, hydrogen is released from the sample at about 141 degrees C. as indicated by the increase in partial pressure as recorded by the residual gas analyzer.

Figure 5:
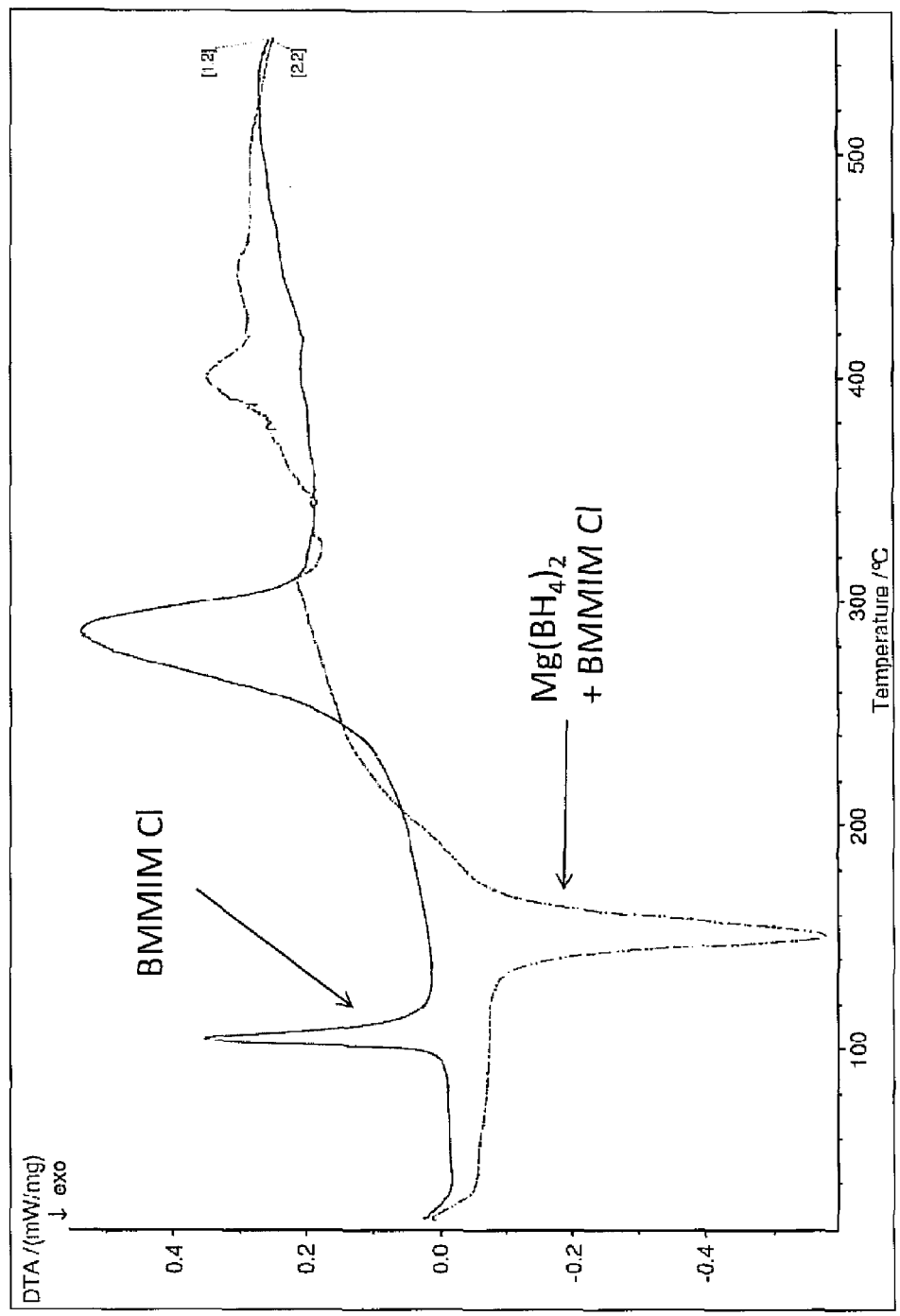
FIG. 5 is a plot of the the energy changes as a function of temperature for an ionic liquid (1-butyl-2,3-dimethylimidazolium chloride) and magnesium borohydride in an ionic liquid (1-butyl-2,3-dimethylimidazolium chloride).

Referring to FIG. 5, there is shown a plot of the energy changes for both the ionic liquid and of a combined sample that was prepared as described above. As can be seen from the plot, the ionic liquid has an endotherm corresponding to the melting of the sample. The combined sample does not have an endotherm confirming that the sample is a liquid or paste at room temperature.

Although a preferred description of the invention has been described, it is for illustrative purposes only. The words used are descriptive rather than of limitative form.

The invention claimed is:

1. A hydrogen release material comprising:
   a complex metal hydride;
   an ionic liquid wherein the hydrogen release material has a lower hydrogen release temperature in comparison to the complex metal hydride alone and
   wherein the ionic liquid includes a member selected from the group consisting of N,N' imidazolium, N-pyridinium, pyridinium or pipperidinium cations with an anion including at least one of $AlCl_4^-$, $Al_2Cl_7^-$, $PF_6^-$, $BF_4^-$, $Cl^-$ or $CF_3SO_3^-$, and combinations thereof.

2. The hydrogen release material of claim 1 wherein the hydrogen release material has a faster hydrogen release rate in comparison to the complex metal hydride alone.

3. The hydrogen release material of claim 1 wherein the hydrogen release material has a more mobile and less stable complex hydride anion which lowers an activation barrier for hydrogen release in comparison to the complex metal hydride alone.

4. The hydrogen release material of claim 1 wherein the complex metal hydride has a formula of $M(BH_4)_x$ where M is an alkali metal, an alkaline earth metal or a transition metal and $1 \leq x \leq 2$.

5. The hydrogen release material of claim 1 wherein the complex metal hydride has a formula of $M(AlH_4)_x$ where $1 \leq x \leq 2$ and where M is an alkali metal, an alkaline earth metal or a transition metal.

6. The hydrogen release material of claim 1 wherein the complex metal hydride is selected from the group consisting of: magnesium borohydride, sodium borohydride, potassium borohydride, lithium borohydride and combinations thereof.

7. The hydrogen release material of claim 1 wherein the complex metal hydride cation is selected from the group consisting of: magnesium, calcium, strontium, barium, and mixtures thereof.

8. The hydrogen release material of claim 1 wherein the complex metal hydride has the formula $M(AlH_4)_x$, wherein M is an alkali metal, an alkaline earth metal or a transition metal and the complex metal hydride is selected from the group consisting of $LiAlH_4$, $NaAlH_4$, $Mg(AlH_4)_2$ and $Ca(AlH_4)_2$.

9. The hydrogen release material of claim 1 wherein the complex metal hydride is solubilized in the ionic liquid forming cations and anions.

10. The hydrogen release material of claim 1 wherein when a solid complex metal hydride when combined with a solid ionic liquid forms a paste or liquid at room temperature.

11. The hydrogen release material of claim 1 wherein the hydrogen release material is capable of reversible storage and release of hydrogen.

12. The hydrogen release material of claim 1 wherein the ionic liquid is present in an amount of 5 to 60 weight percent based on a total weight of a mixture.

13. The hydrogen release material of claim 1 wherein the combined ionic liquid and metal hydride form a liquid or a paste at room temperature.

14. A process of releasing hydrogen from a storage material including the steps of:
providing a complex metal hydride;
combining the complex metal hydride with an ionic liquid in a desired amount forming a mixture, wherein the ionic liquid includes a member selected from the group consisting of N,N' imidazolium, N-pyridinium, pyridinium or pipperidinium cations with an anion including at least one of $AlCl_4^-$, $Al_2Cl_7^-$, $PF_6^-$, $BF_4^-$, $Cl^-$ or $CF_3SO_3^-$, and combinations thereof; and
heating the mixture to a temperature releasing hydrogen wherein the temperature is lower in comparison to the complex metal hydride alone.

15. The process of releasing hydrogen from a storage material of claim 14 including grinding the complex metal hydride.

16. The process of releasing hydrogen from a storage material of claim 14 wherein the combining step includes grinding the complex metal hydride and the ionic liquid.

17. The process of releasing hydrogen from a storage material of claim 16 wherein the ionic liquid melts followed by hydrogen release.

18. The process of releasing hydrogen from a storage material of claim 14 wherein the ionic liquid solubilizes the complex metal hydride lessening hydrogen reaction diffusion limitations of a solid complex metal hydride material.

19. The process of releasing hydrogen from a storage material of claim 14 wherein when a solid complex metal hydride when combined with a solid ionic liquid forms a paste or liquid at room temperature.

20. The process of releasing hydrogen from a storage material of claim 14 including a step of recharging the hydrogen release material with hydrogen after release.

21. The process of releasing hydrogen from a storage material of claim 20 wherein the recharging step occurs at a temperature and pressure lower than the complex metal hydride alone.

22. The process of releasing hydrogen from a storage material of claim 20 wherein the recharging step occurs faster in comparison to the complex metal hydride alone.

23. The process of releasing hydrogen from a storage material of claim 20 wherein the recharging step has a reduced activation barrier for hydrogen in comparison to the complex metal hydride alone.

24. The process of releasing hydrogen from a storage material of claim 20 including a step of drying the ionic liquid by removing water prior to combining with the metal hydride.

25. The process of claim 14 wherein the combined ionic liquid and metal hydride form a liquid or a paste at room temperature.

* * * * *